(12) United States Patent
Mihara

(10) Patent No.: US 10,267,772 B2
(45) Date of Patent: Apr. 23, 2019

(54) HAIR MOISTURE MEASURING DEVICE, AND METHODS OF MAKING AND USING THE DEVICE

(71) Applicant: EMPIRE TECHNOLOGY DEVELOPMENT LLC, Wilmington, DE (US)

(72) Inventor: Masaaki Mihara, Chiba (JP)

(73) Assignee: Empire Technology Development LLC, Wilmington, DE (US)

( * ) Notice: Subject to any disclaimer, the term of this patent is extended or adjusted under 35 U.S.C. 154(b) by 182 days.

(21) Appl. No.: 15/121,012

(22) PCT Filed: Mar. 3, 2014

(86) PCT No.: PCT/US2014/019985
§ 371 (c)(1),
(2) Date: Aug. 23, 2016

(87) PCT Pub. No.: WO2015/133993
PCT Pub. Date: Sep. 11, 2015

(65) Prior Publication Data
US 2017/0023528 A1  Jan. 26, 2017

(51) Int. Cl.
*G01N 29/07* (2006.01)

(52) U.S. Cl.
CPC ....... *G01N 29/07* (2013.01); *G01N 2291/011* (2013.01); *G01N 2291/02845* (2013.01)

(58) Field of Classification Search
CPC ............. G01N 29/07; G01N 2291/011; G01N 2291/02845; G01N 2800/20; A61B 5/441; A61B 5/448; A61B 5/6838; A61B 2018/00452; A61B 2018/00476; A61B 5/0051; A61B 5/0059; A61B 5/443; A61B 5/7282; A61B 5/742; A61B 2017/00876; A61B 2503/40; A61B 2562/12
(Continued)

(56) References Cited

U.S. PATENT DOCUMENTS

| 3,302,301 A | 2/1967 | Goble |
| 4,258,731 A | 3/1981 | Tsujimoto et al. |

(Continued)

OTHER PUBLICATIONS

International Search Report and Written Opinion for International Application No. PCT/US2014/019985 dated Jun. 20, 2014, pp. 17.

*Primary Examiner* — Lisa M Caputo
*Assistant Examiner* — Suman K Nath

(57) ABSTRACT

Technologies are generally described for measuring hair moisture using a hair moisture measuring device including a vibrator, a sound wave detector, a heater, and/or a processor. The vibrator may generate and propagate first sound waves through a strand of hair, which may be detected by the sound wave detector. The processor may then measure a first time-delay between the first sound waves and the first driving signals. After heating the hair by the heater, the vibrator may generate and propagate second sound waves through the strand of hair, which may be detected by the sound wave detector. The processor may measure a second time-delay between the second sound waves and the second driving signals, and also measure an amount of the moisture by calculating a time-delay difference between the first time-delay and the second time-delay.

34 Claims, 10 Drawing Sheets

(58) Field of Classification Search
USPC .............. 73/597, 760, 788, 800; 356/238.1, 356/432–440, 428–431; 132/203, 207, 132/212
See application file for complete search history.

(56) References Cited

U.S. PATENT DOCUMENTS

| | | |
|---|---|---|
| 4,744,154 A | 5/1988 | Bollinger et al. |
| 5,568,818 A | 10/1996 | Neri et al. |
| 6,026,821 A | 2/2000 | Last |
| 7,928,739 B2 | 4/2011 | Sherman et al. |
| 9,855,004 B2 * | 1/2018 | Mihara .................. A61B 5/448 |
| 2009/0025247 A1 | 1/2009 | Yde et al. |
| 2010/0042007 A1 | 2/2010 | Blanco et al. |
| 2010/0043708 A1 | 2/2010 | Choi et al. |
| 2010/0237057 A1 | 9/2010 | Hafemann |
| 2011/0120491 A1 | 5/2011 | You |
| 2011/0209721 A1 | 9/2011 | Yahnker et al. |
| 2012/0041282 A1 | 2/2012 | Nichol et al. |
| 2013/0345620 A1 | 12/2013 | Zemel et al. |

\* cited by examiner

HAIR MOISTURE MEASURING DEVICE, AND METHODS OF MAKING AND USING THE DEVICE

RELATED APPLICATIONS

This application is a U.S. National Stage filing under 35 U.S.C. § 371 of PCT Application No. PCT/US2014/019985, filed Mar. 3, 2014 which application is incorporated herein by reference in its entirety, for any purpose.

BACKGROUND

Unless otherwise indicated herein, the approaches described in this section are not prior art to the claims in this application and are not admitted to be prior art by inclusion in this section.

Substances such as hair are hygroscopic and permeable, such that they can absorb moisture from the environment. For example, hair typically contains moisture accounting for about 12% to about 15% of the total weight. The hygroscopic property of hair determines the health of the hair, which can then determine available styling options for the hair. The capability of hair for retaining moisture can be deteriorated when it is damaged through styling such as a hair perm, exposure to hair styling products and exposure to hair dyes. Accordingly, it is important to precisely measure hair moisture to determine the overall health of hair or the moisture content in hair so that once can assess possible styling options and hair care options to maintain or improve the health of the hair.

Hair moisture measuring devices have been developed to detect the moisture level in hair, and have employed various techniques including a NIR (near infrared) moisture meter and Raman spectroscopy. The NIR moisture meter relies on the property of water that absorbs a specific wavelength of NIR light. However, it may be difficult to precisely measure the attenuation of the NIR light reflected from thin and fine hairs. Also, different levels of moisture at the surface and inner side of hair make the moisture measurement more challenging. The Raman spectroscopy relies on inelastic scattering of monochromatic light such as laser light irradiated on molecules of moisture in hair. For example, the laser light interacts with molecular vibrations, resulting in the energy of the laser photons being shifted upwards or downwards between a ground energy state and a virtual energy state. The shift in energy provides information about the vibrational modes to identify the molecules of moisture. Although the Raman spectroscopy provides decent precision of moisture measurement, it is costly and may not be implemented in a portable size for individual users.

SUMMARY

Technologies generally described herein relate to measuring moisture in hair.

Various example apparatus configured to measure hair moisture described herein may include one or more of at least one vibrator, at least one sound wave detector, at least one heater, and/or a processor. The at least one vibrator may be configured to generate sound waves in response to driving signals, and to propagate the sound waves through at least one strand of hair before and after moisture removal. The at least one sound wave detector may be spaced apart from the vibrator, and may be configured to detect the sound waves that have propagated through the hair. The at least one heater may be configured to generate heat for at least partially removing moisture in the hair. The processor may be configured to generate the driving signals that are fed to the vibrator, and to measure a time-delay between the sound waves and the driving signals.

In some examples, methods for measuring hair moisture are described. Example methods may include propagating first sound waves through at least one strand of hair, detecting the first sound waves that have propagated through the hair, and measuring a first time-delay between the first sound waves and first driving signals that are used to generate the first sound waves. The hair may be heated to at least partially remove moisture from the hair. The methods may further include propagating second sound waves through the at least one strand of hair after heating, detecting the second sound waves that have propagated through the hair, and measuring a second time-delay between the second sound waves and second driving signals that are used to generate the second sound waves. An amount of the moisture may be measured by calculating a time-delay difference between the first time-delay and the second time-delay.

In some examples, a computer-readable storage medium is described that may be adapted to store a program operable by a hair moisture measuring device. The processor may include various features as further described herein. The program may include one or more instructions for propagating first sound waves through at least one strand of hair, detecting the first sound waves that have propagated through the hair, measuring a first time-delay between the first sound waves first driving signals that are used to generate the first sound waves, and heating the hair to at least partially remove moisture from the hair. The program may further include one or more instructions for propagating second sound waves through at least one strand of hair after heating, detecting the second sound waves that have propagated through the hair, measuring a second time-delay between the second sound waves and second driving signals that are used to generate the second sound waves, and measuring an amount of the moisture by calculating a time-delay difference between the first time-delay and second time-delay.

In some examples, methods of measuring hair moisture using a hair moisture measuring device are described. The hair moisture measuring device may include one or more of at least one vibrator, at least one sound wave detector, at least one heater, and/or a processor. The at least one vibrator may be configured to generate sound waves in response to driving signals, and to propagate the sound waves through at least one strand of hair before and after moisture removal. The at least one sound wave detector may be spaced apart from the vibrator, and may be configured to detect the sound waves that have propagated through the hair. The at least one heater may be configured to generate heat for at least partially removing moisture in the hair. The processor may be configured to generate the driving signals that are fed to the vibrator, and to measure a time-delay between the sound waves and the driving signals.

In some examples, methods of manufacturing a hair moisture measuring device are described. Example methods may include preparing a substrate. At least one vibrator may be disposed on a first end of the substrate, the vibrator being configured to generate sound waves in response to driving signals, and to propagate the sound waves through at least one strand of hair before and after moisture removal. At least one sound wave detector may be disposed on a second end of the substrate, such that the sound wave detector is spaced apart from the vibrator, the sound wave detector being configured to detect the sound waves that have propagated through the hair. At least one heater may be disposed on the substrate, such that the heater is disposed between the vibrator and the sound wave detector, the heater being configured to generate heat for at least partially removing moisture in the hair. A processor may be coupled to the vibrator, the sound wave detector and the heater, the processor being configured to generate the driving signals that are fed to the vibrator, and to measure a time-delay between the sound waves and the driving signals.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
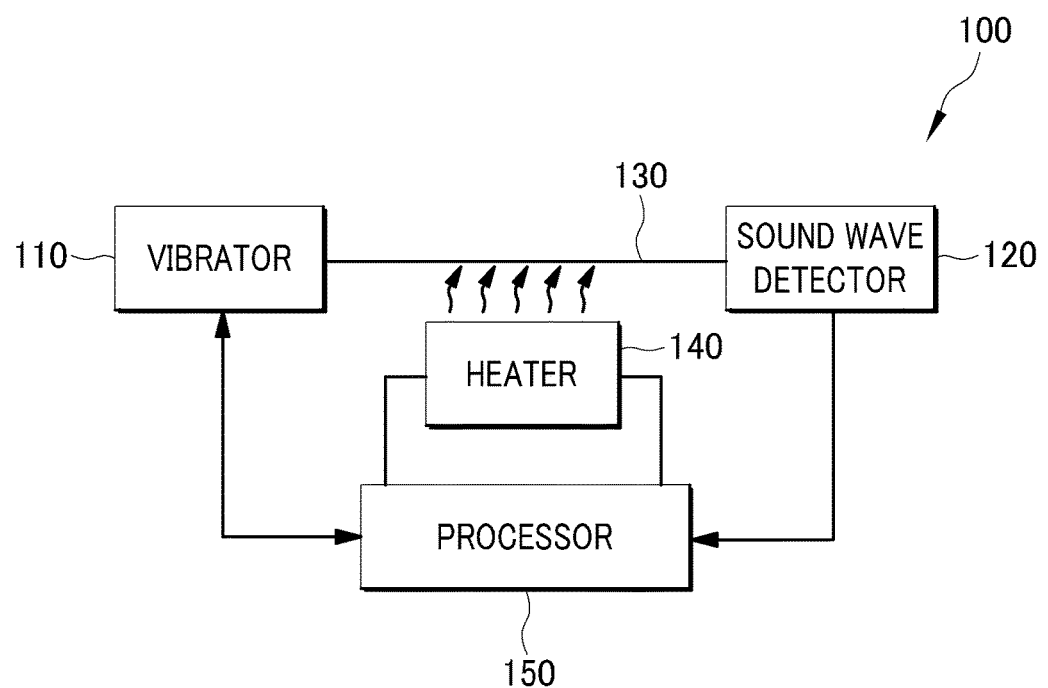
FIG. 1 schematically shows a block diagram of an example hair moisture measuring device configured to measure moisture in hair by detecting time-delays of sound waves propagated through the hair.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices and computer program products related to measuring moisture in hair.

Briefly stated, technologies are generally described for measuring hair moisture using a hair moisture measuring device. Example devices/systems described herein may include one or more of a vibrator, a sound wave detector, a heater, and/or a processor. The vibrator may generate first sound waves in response to first driving signals that may be provided from the processor, and propagate the first sound waves through a strand of hair. The sound wave detector may detect the first sound waves that have propagated through the hair. The processor may then measure a first time-delay between the first sound waves and the first driving signals. The heater may generate heat for at least partially removing moisture in the hair. After heating the hair, the vibrator may generate second sound waves in response to second driving signals that may be provided from the processor, and propagate the second sound waves through the strand of hair. The sound wave detector may detect the second sound waves that have propagated through the hair. The processor may measure a second time-delay between the second sound waves and the second driving signals. Further, the processor may measure an amount of the moisture by calculating a time-delay difference between the first time-delay and the second time-delay.

FIG. 1 schematically shows a block diagram of an example hair moisture measuring device configured to measure moisture in hair by detecting time-delays of sound waves propagated through the hair, arranged in accordance with at least some embodiments described herein. As depicted, a hair moisture measuring device 100 may include one or more of a vibrator 110, a sound wave detector 120, a heater 140 and/or a processor 150.

In some embodiments, vibrator 110 may be coupled to sound wave detector 120 through a strand of hair 130. In particular, one end of the strand of hair 130 may be coupled to an output of vibrator 110, while the other end of the strand of hair 130 may be coupled to an input of sound wave detector 120. In some embodiments, a first hair clamp (not shown) may be arranged at a side of vibrator 110, which may be disposed at one end of device 100, and configured to clamp one end of hair 130. Further, a second hair clamp (not shown) may be arranged at a side of sound wave detector 120, which may be disposed at the other end of device 100, and configured to clamp the other end of hair 130 so that hair 130 is stretched between the first and second hair clamps. In some embodiments, hair 130 may be a human hair or an animal hair such as wool, mohair, cashmere, angora, fleece, fur or a combination thereof.

In some embodiments, vibrator 110 may include an ultrasonic vibrator, such as an ultrasonic ceramic transducer, configured to generate ultrasonic sound waves. Also, sound wave detector 120 may include an ultrasonic microphone, such as an ultrasonic ceramic transducer, configured to detect ultrasonic sound waves.

In some embodiments, heater 140 may be disposed between vibrator 110 and sound wave detector 120 such that heater 140 may generate heat towards substantially at least a portion of hair 130. Heater 140 may include a ceramic material and at least one heating wire embedded in the ceramic material. In this case, heater 140 may be configured to generate heat by passing electricity through the heating wires embedded in the ceramic material, in which the electricity may be provided from processor 150. Alternatively, heater 140 may include one or more infrared LEDs (light-emitting diodes). Heater 140 may generate heat by providing electricity to the LEDs so that the LEDs irradiate infrared light, in which the electricity may be provided from processor 150.

In operation, vibrator 110 may be configured to generate sound waves in response to driving signals that may be provided from processor 150, and configured to propagate the sound waves through the strand of hair 130 before and after moisture removal. In some embodiments, vibrator 110 may generate first sound waves in response to first driving signals that may be provided from processor 150, and propagate the first sound waves through the strand of hair 130. Vibrator 110 may receive driving signals from processor 150 to generate sound waves at regular intervals in a burst shape (for example, intermittent signals).

In some embodiments, sound wave detector 120 may be configured to detect the first sound waves that have propagated through hair 130. Processor 150 may be configured to measure a first time-delay between the first sound waves and the first driving signals. During propagation of the sound waves through hair 130, a time-delay may occur between a first time, substantially when the first driving signals are transmitted from vibrator 110, and a second time, substantially when the first sound waves that have propagated through hair 130 are detected by sound wave detector 120. Such time-delay may depend on a length of hair 130 and/or a property of hair 130 such as moisture level. In case the sound waves are generated in a burst fashion, processor 150 may measure the first time-delay based on the burst timing of the first driving signals and first sound waves.

In some embodiments, heater 140 may be configured to generate heat for at least partially evaporating or removing moisture in hair 130. Hair 130 may be heated for a predetermined period of time at a predetermined temperature, which may be not greater than a temperature at which hair 130 may denature. For example, hair 130 may be heated for about 120 seconds at 60 degrees Celsius or less.

In some embodiments, after heating hair 130, vibrator 110 may generate second sound waves in response to second driving signals that may be provided from processor 150, and propagate the second sound waves through the strand of hair 130. Sound wave detector 120 may then detect the second sound waves that have propagated through hair 130. Processor 150 may measure a second time-delay between the second sound waves and the second driving signals. Further, processor 150 may measure an amount of the moisture by calculating a time-delay difference between the first time-delay and the second time-delay. As such, processor 150 may measure an amount of the moisture in hair 130 by comparing the first time-delay between the first driving signals and the first sound waves, which is detected for hair 130 prior to being heated by heater 140, and the second time-delay between the second driving signals and the second sound waves, which is detected for hair 130 after being heated by heater 140.

In some embodiments, a difference between the first and second time-delays may be compared with a reference, which may be pre-stored in a memory unit (not shown) of hair moisture measuring device 100. The reference may be represented as a calibration curve (or a look-up table), in which an x axis (or a first column) indicates time-delay differences and a y axis (or a second column) indicates associated moisture contents. Thus, if a time delay difference (for example, a difference between the first and second time-delays) is measured as described above, an associated moisture content may be found by looking up the time delay difference in the reference. For example, a look-up table including the reference may be pre-stored in the memory unit. Processor 150 may determine the amount of moisture contained in hair 130 by identifying the time-delay difference in the reference that best matches the time-delay difference between the first time-delay and the second time-delay.

In some embodiments, a reference including time-delay differences and associated moisture contents may be prepared for a predetermined exemplary hair type. Because hair may have different properties (for example, thickness, hygroscopicity, water retention property, etc.) for different human races or different animals, a reference may be prepared for each of the human races or different animals. For example, a collection of hair may be sampled from a group of persons belonging to a same human race with substantially same hair health condition. For preparation of a reference, various collections of hair may be sampled from the same group of persons in different environments (for example, different atmosphere temperatures and humidity). The weight of each collection of hair may be measured before and after heating the hair to remove moisture from the hair. By comparing the weights of the hair measured before and after heating, an average moisture content for the collected hair may be determined. In addition, a time delay difference may be measured for each collection of hair in a manner as described above. Thus, a reference may be prepared by associating the measured time delay differences with moisture contents determined for different hair health conditions and/or different environments.

In some embodiments, processor 150 may include a microprocessor, a signal generator configured to generate the driving signals, an oscilloscope configured to measure and/or display the sound waves, the time delays, or a combination thereof. Also, device 100 may further include a display unit (not shown) electrically coupled to processor 150 and configured to display at least one of the driving signals, the sound waves, and the measured time delays.

Figure 2:
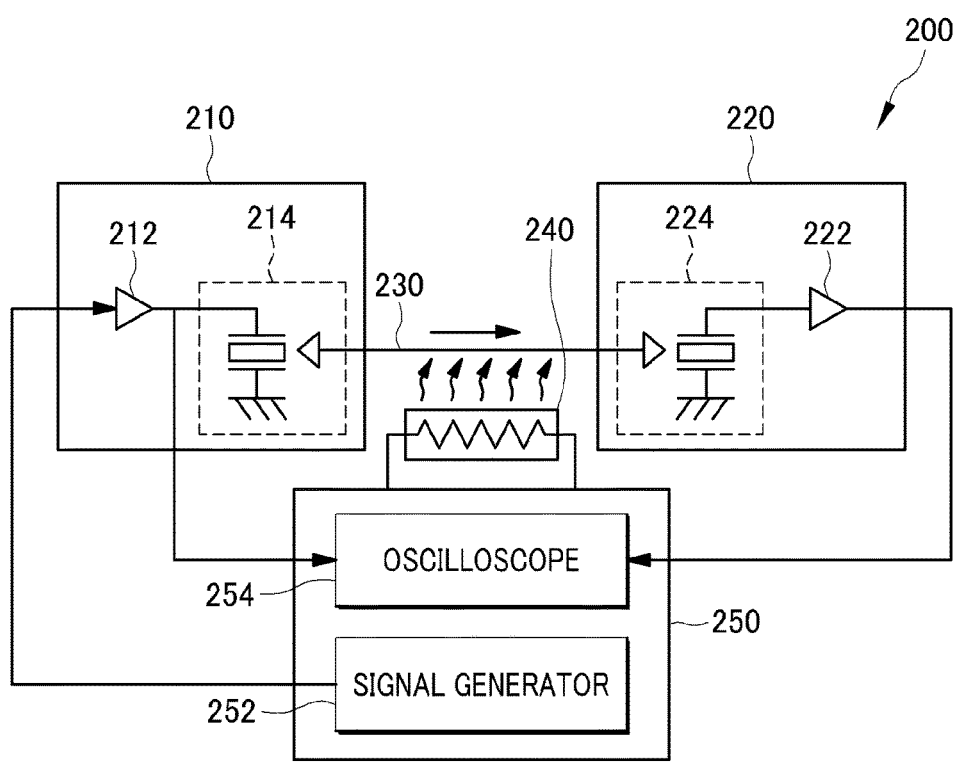
FIG. 2 schematically shows a block diagram of another example hair moisture measuring device configured to measure moisture in hair by detecting time-delays of sound waves propagated through the hair.

FIG. 2 schematically shows a block diagram of another example hair moisture measuring device configured to measure moisture in hair by detecting time-delays of sound waves propagated through the hair, arranged in accordance with at least some embodiments described herein. As depicted, a hair moisture measuring device 200 may include one or more of a vibrator 210, a sound wave detector 220, a heater 240 and/or a processor 250. In some embodiments, vibrator 210 may be coupled to sound wave detector 220 through a strand of hair 230. In particular, one end of the strand of hair 230 may be coupled to an output of vibrator 210, while the other end of the strand of hair 230 may be coupled to an input of sound wave detector 220.

In some embodiments, vibrator 210 may include a driver circuit 212 configured to receive driving signals from processor 250 and configured to generate voltages according to the driving signals. Vibrator 210 may further include an ultrasonic transducer 214 configured to receive the voltages from driver circuit 212 and generate ultrasonic sound waves according to the voltages. Ultrasonic transducer 214 may be a piezoelectric transducer including piezoelectric crystals having the property of changing size when the voltages are applied, and thus oscillating at ultrasonic frequencies. On the other hand, sound wave detector 220 may include an ultrasonic transducer 224 configured to receive ultrasonic sound waves that have propagated through the strand of hair 230 and generate voltages in response to the ultrasonic sound waves. Again, ultrasonic transducer 224 may be a piezoelectric transducer including piezoelectric crystals having the property of generating voltages when force according to the sound waves is applied. Sound wave detector 220 may further include an amplifier 222 configured to amplify the voltages from ultrasonic transducer 224 for providing to processor 250.

In some embodiments, heater 240 may be disposed between vibrator 210 and sound wave detector 220. For example, heater 240 may be a ceramic heater configured to generate heat by passing electricity through heating wires embedded in a ceramic material, in which the electricity may be provided from processor 250. In some other examples, heater 240 may be a sheet heater configured to generate heat by passing electricity through heating wires embedded in two sheets (for example, made of silicon or polyimide) attached to each other. Alternatively, heater 140 may include one or more infrared LEDs configured to generate infrared light in response to the electricity provided from processor 250.

In some embodiments, processor 250 may include a signal generator 252 configured to generate driving signals for providing to vibrator 210. For example, signal generator 252 may be an oscillator configured to generate pulse signals or intermittent signals in a burst shape as the driving signals. Also, processor 250 may include an oscilloscope 254 configured to receive voltages from vibrator 210 and/or sound wave detector 220 and display the change of voltages over time on a display unit (not shown) for a user or an operator.

In operation, vibrator 210 may be configured to generate ultrasonic sound waves in response to driving signals that may be provided from processor 250, and configured to propagate the ultrasonic sound waves through the strand of hair 230 before and after moisture removal. In some embodiments, vibrator 210 may generate first ultrasonic sound waves in response to first driving signals that may be provided from processor 250, and propagate the first ultrasonic sound waves through the strand of hair 230. Vibrator 210 may receive driving signals from processor 250 to generate ultrasonic sound waves at regular intervals in a burst shape (for example, intermittent signals).

In some embodiments, sound wave detector 220 may be configured to detect the first ultrasonic sound waves that have propagated through hair 230. Processor 250 may be configured to measure a first time-delay between the first ultrasonic sound waves and the first driving signals. During propagation of the ultrasonic sound waves through hair 230, a time-delay may occur between a first time, substantially when the first driving signals are transmitted from vibrator 210, and a second time, substantially when the first ultrasonic sound waves that have propagated through hair 230 are detected by sound wave detector 220. Such time-delay may depend on a length of hair 230 and/or a property of hair 230 such as moisture level. In case the ultrasonic sound waves are generated in a burst fashion, processor 250 may measure the first time-delay based on the burst timing of the first driving signals and first ultrasonic sound waves.

In some embodiments, heater 240 may be configured to generate heat for at least partially evaporating or removing moisture in hair 230. Hair 230 may be heated for a predetermined period of time at a predetermined temperature, which may be not greater than a temperature at which hair 230 may denature. For example, hair 230 may be heated for about 120 seconds at 60 degrees Celsius or less.

In some embodiments, after heating hair 230, vibrator 210 may generate second ultrasonic sound waves in response to second driving signals that may be provided from processor 250, and propagate the second ultrasonic sound waves through the strand of hair 230. Sound wave detector 220 may then detect the second ultrasonic sound waves that have propagated through hair 230. Processor 250 may measure a second time-delay between the second ultrasonic sound waves and the second driving signals. Further, processor 250 may measure an amount of the moisture by calculating a time-delay difference between the first time-delay and the second time-delay. As such, processor 250 may measure an amount of the moisture in hair 230 by comparing the first time-delay between the first driving signals and the first ultrasonic sound waves, which is detected for hair 230 prior to being heated by heater 240, and the second time-delay between the second driving signals and the second ultrasonic sound waves, which is detected for hair 230 after being heated by heater 240.

In some embodiments, a difference between the first and second time-delays may be compared with a reference, which may be pre-stored in a memory unit (not shown) of hair moisture measuring device 200. The reference may include a list of time-delay differences associated with respective moisture contents. For example, a look-up table including the reference may be pre-stored in the memory unit. The reference time-delay differences and associated moisture contents may be pre-measured for predetermined exemplary hair types (for example, exemplary hair sampled from different races, different animals, etc.). Processor 250 may determine the amount of moisture contained in hair 230 by identifying the time-delay difference in the reference that best matches the time-delay difference between the first time-delay and the second time-delay. Processor 250 may be further configured to display at least one of the driving signals, the ultrasonic sound waves, and the measured time delays on the display unit.

Figure 3A:
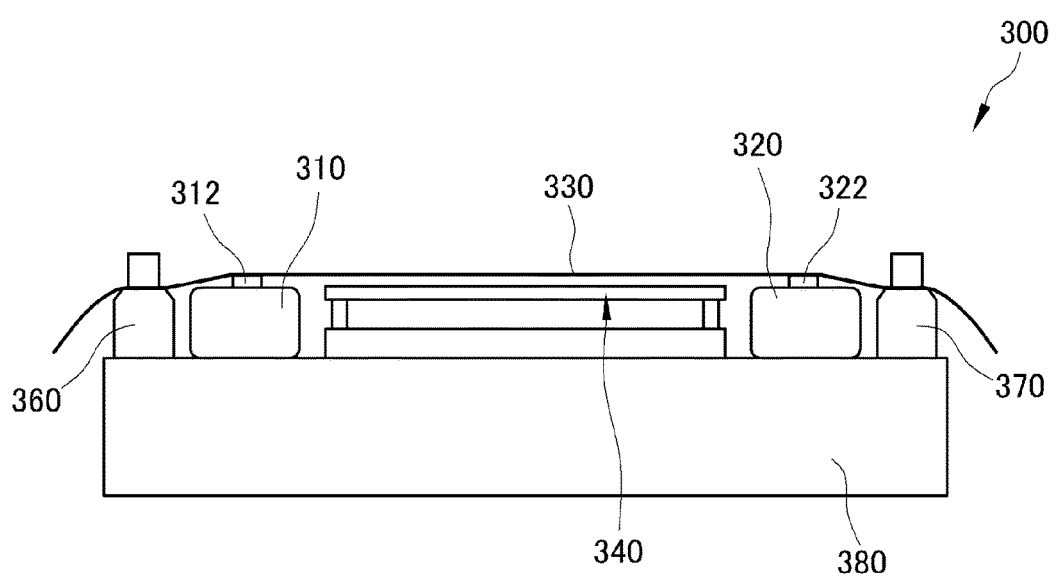
FIGS. 3A and 3B schematically show a front view and a top view of an example hair moisture measuring device including a ceramic heater.
Figure 3B:
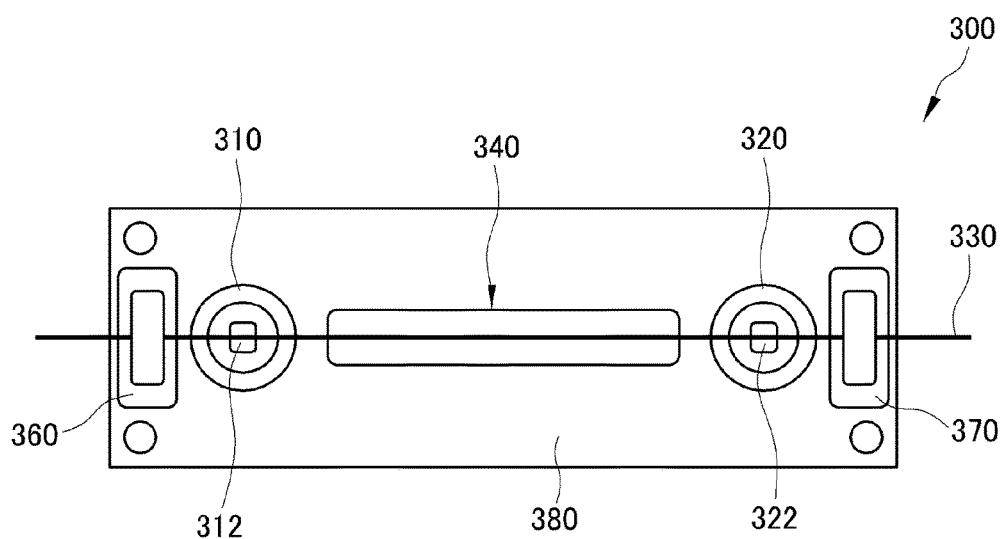

FIGS. 3A and 3B schematically show a front view and a top view of an example hair moisture measuring device including a ceramic heater, arranged in accordance with at least some embodiments described herein. As illustrated, a hair moisture measuring device 300 may include one or more of a vibrator 310, a sound wave detector 320 and/or a ceramic heater 340, which may be disposed on a substrate 380. Although not explicitly illustrated in FIGS. 3A and 3B, device 300 may further include a processor, which may be disposed at an inside of substrate 380. The processor may operate in a similar manner as described above with respect to processor 150 or 250.

In some embodiments, vibrator 310 may be coupled to sound wave detector 320 through a strand of hair 330. As depicted in FIG. 3A, one end of the strand of hair 330 may be coupled to an output 312 of vibrator 310, while the other end of the strand of hair 330 may be coupled to an input 322 of sound wave detector 320. Further, a first hair clamp 360 may be arranged in the vicinity of vibrator 310, which may be disposed at one end of substrate 380, and configured to clamp one end of hair 330. Further, a second hair clamp 370 may be arranged in the vicinity of sound wave detector 320, which may be disposed at the other end of substrate 380, and configured to clamp the other end of hair 330 so that hair 330 is stretched between first and second hair clamps 360 and 370.

In some embodiments, vibrator 310 may include an ultrasonic vibrator, such as an ultrasonic ceramic transducer, configured to generate ultrasonic sound waves. Also, sound wave detector 320 may include an ultrasonic microphone, such as an ultrasonic ceramic transducer, configured to detect ultrasonic sound waves.

In some embodiments, ceramic heater 340 may be disposed between vibrator 310 and sound wave detector 320 on substrate 380. Ceramic heater 340 may include a ceramic material and at least one heating wire embedded in the ceramic material. Ceramic heater 340 may generate heat by passing electricity through the heating wires embedded in the ceramic material, in which the electricity may be provided from the processor.

Hair moisture measuring device 300 may operate in a similar manner as device 100 or 200 described above with reference to FIGS. 1 and 2. More specifically, vibrator 310 may propagate first sound waves through the strand of hair 330, and sound wave detector 320 may detect the first sound waves that have propagated through hair 330. The processor may measure a first time-delay between the first sound waves and first driving signals that are used to generate the first sound waves. Further, heater 340 may heat hair 330 to at least partially remove moisture from hair 330. After heating hair 330, vibrator 310 may propagate second sound waves through the strand of hair 330, and sound wave detector 320 may detect the second sound waves that have propagated through hair 330. Again, the processor may measure a second time-delay between the second sound waves and second driving signals that are used to generate the second sound waves. An amount of the moisture may be measured by calculating a time-delay difference between the first time-delay and the second time-delay.

Figure 4A:
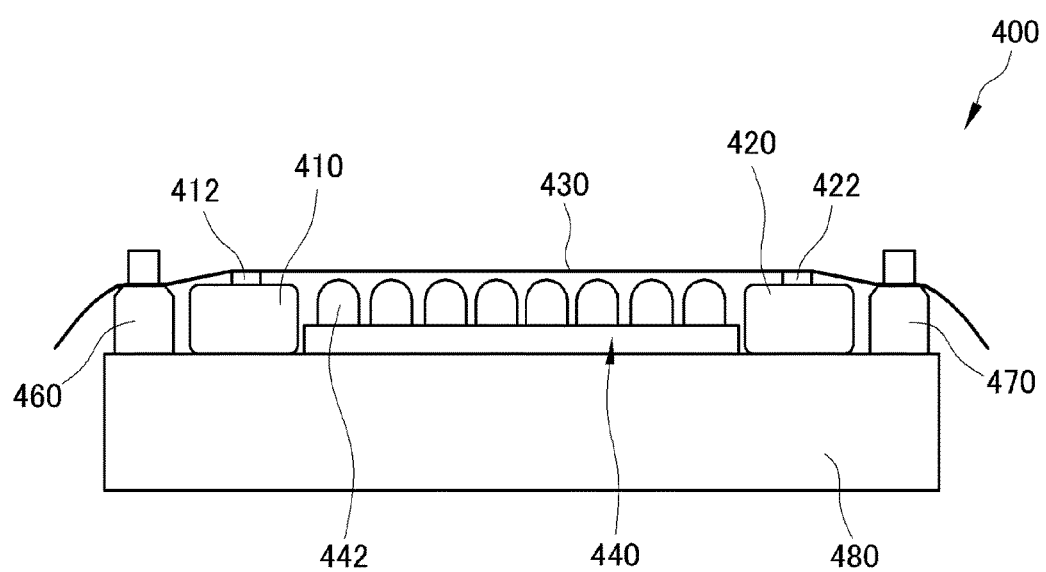
FIGS. 4A and 4B schematically show a front view and a top view of an example hair moisture measuring device including a heater including one or more infrared LEDs.
Figure 4B:
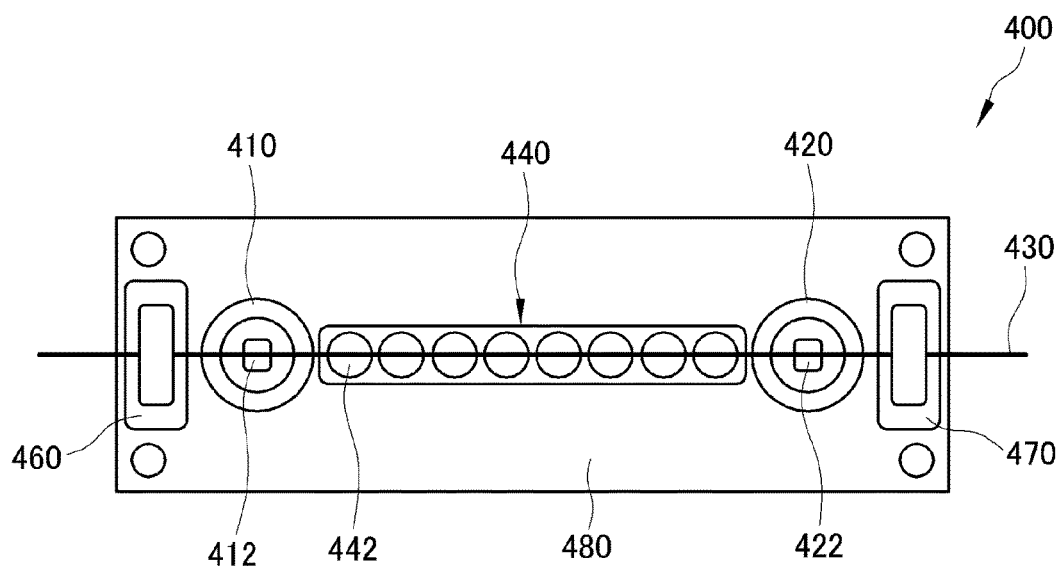

FIGS. 4A and 4B schematically show a front view and a top view of an example hair moisture measuring device including a heater including one or more infrared LEDs, arranged in accordance with at least some embodiments described herein. As illustrated, a hair moisture measuring device 400 may include one or more of a vibrator 410, a sound wave detector 420 and/or a heater 440 including one or more infrared LEDs, which may be disposed on a substrate 480. Although not explicitly illustrated in FIGS. 4A and 4B, device 400 may further include a processor, which may be disposed at an inside of substrate 480. The processor may operate in a similar manner as described above with respect to processor 150 or 250.

In some embodiments, vibrator 410 may be coupled to sound wave detector 420 through a strand of hair 430. As depicted in FIG. 4A, one end of the strand of hair 430 may be coupled to an output 412 of vibrator 410, while the other end of the strand of hair 430 may be coupled to an input 422 of sound wave detector 420. Further, a first hair clamp 460 may be arranged in the vicinity of vibrator 410, which may be disposed at one end of substrate 480, and configured to clamp one end of hair 430. Further, a second hair clamp 470 may be arranged in the vicinity of sound wave detector 420, which may be disposed at the other end of substrate 480, and configured to clamp the other end of hair 430 so that hair 430 is stretched between first and second hair clamps 460 and 470.

In some embodiments, vibrator 410 may include an ultrasonic vibrator, such as an ultrasonic ceramic transducer, configured to generate ultrasonic sound waves. Also, sound wave detector 420 may include an ultrasonic microphone, such as an ultrasonic ceramic transducer, configured to detect ultrasonic sound waves.

In some embodiments, a heater 440 may be disposed between vibrator 410 and sound wave detector 420 on substrate 480. Heater 440 may include one or more infrared LEDs 442. Heater 440 may generate heat by providing electricity to LEDs 442 so that LEDs 442 irradiate infrared light, in which the electricity may be provided from the processor.

Hair moisture measuring device 400 may operate in a similar manner as device 100 or 200 described above with reference to FIGS. 1 and 2. More specifically, vibrator 410 may propagate first sound waves through the strand of hair 430, and sound wave detector 420 may detect the first sound waves that have propagated through hair 430. The processor may measure a first time-delay between the first sound waves and first driving signals that are used to generate the first sound waves. Further, heater 440 may heat hair 430 to at least partially remove moisture from hair 430. After heating hair 430, vibrator 410 may propagate second sound waves through the strand of hair 430, and sound wave detector 420 may detect the second sound waves that have propagated through hair 430. Again, the processor may measure a second time-delay between the second sound waves and second driving signals that are used to generate the second sound waves. An amount of the moisture may be measured by calculating a time-delay difference between the first time-delay and the second time-delay.

Figure 5:
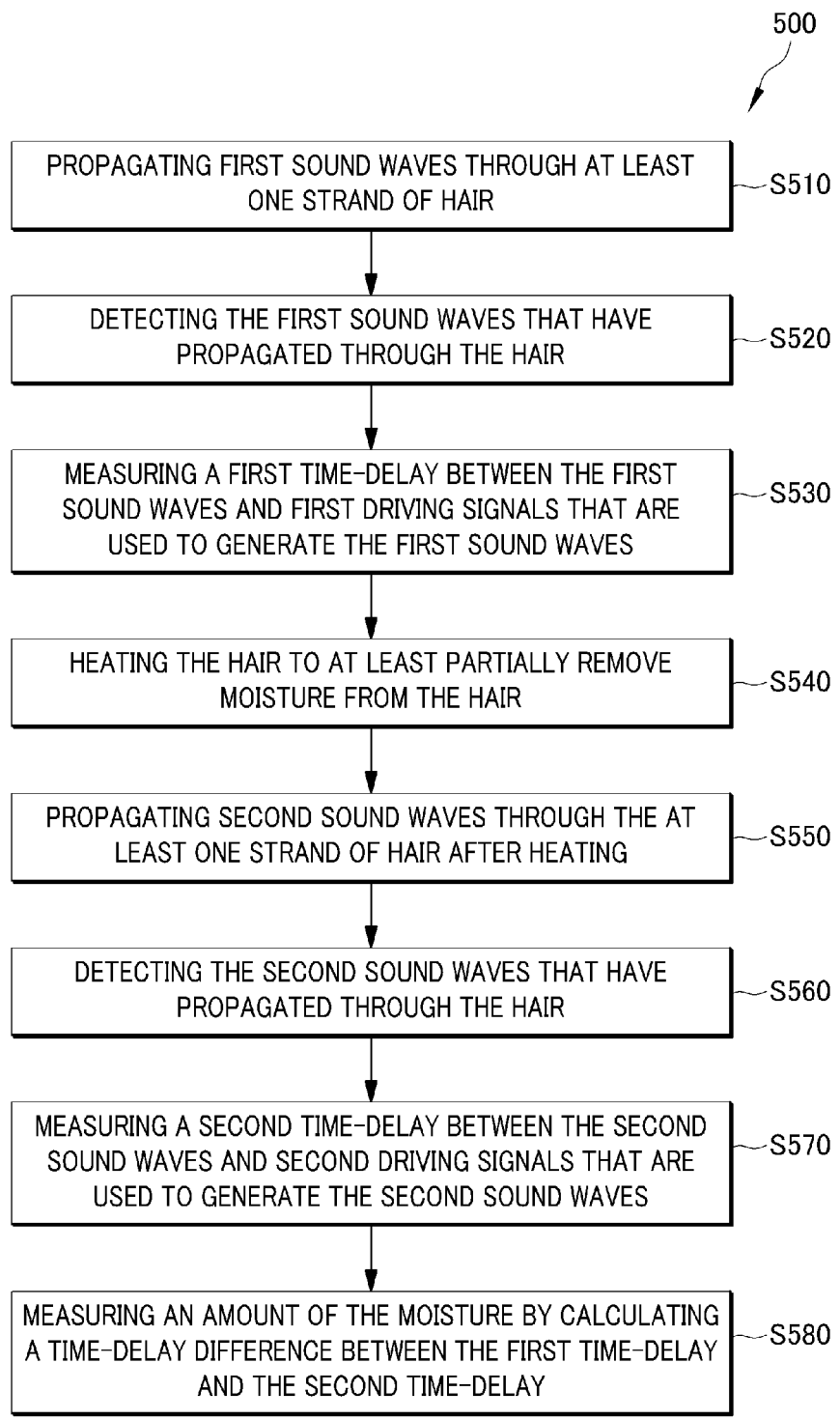
FIG. 5 illustrates an example flow diagram of a method adapted to measure hair moisture.

FIG. 5 illustrates an example flow diagram of a method adapted to measure hair moisture, arranged in accordance with at least some embodiments described herein. An example method 500 in FIG. 5 may be implemented using, for example, a computing device including a processor adapted to measure moisture in hair.

Method 500 may include one or more operations, actions, or functions as illustrated by one or more of blocks S510, S520, S530, S540, S550, S560, S570 and/or S580. Although illustrated as discrete blocks, various blocks may be divided into additional blocks, combined into fewer blocks, or eliminated, depending on the desired implementation. In some further examples, the various described blocks may be implemented as a parallel process instead of a sequential process, or as a combination thereof. Method 500 may begin at block S510, "PROPAGATING FIRST SOUND WAVES THROUGH AT LEAST ONE STRAND OF HAIR."

At block S510, first sound waves may be propagated through at least one strand of hair. As depicted in FIG. 1, vibrator 110 may generate first sound waves in response to first driving signals that may be provided from processor 150, and propagate the first sound waves through the strand of hair 130. Vibrator 110 may receive driving signals from processor 150 to generate sound waves at regular intervals in a burst shape (for example, intermittent signals). In some embodiments, vibrator 110 may include an ultrasonic vibrator, such as an ultrasonic ceramic transducer, configured to generate ultrasonic sound waves. Block S510 may be followed by block S520, "DETECTING THE FIRST SOUND WAVES THAT HAVE PROPAGATED THROUGH THE HAIR."

At block S520, the first sound waves that have propagated through the hair may be detected. As illustrated in FIG. 1, sound wave detector 120 may detect the first sound waves that have propagated through hair 130. In some embodiments, sound wave detector 120 may include an ultrasonic microphone, such as an ultrasonic ceramic transducer, configured to detect ultrasonic sound waves. Block S520 may be followed by block S530, "MEASURING A FIRST TIME-DELAY BETWEEN THE FIRST SOUND WAVES AND FIRST DRIVING SIGNALS THAT ARE USED TO GENERATE THE FIRST SOUND WAVES."

At block S530, a first time-delay may be measured between the first sound waves and first driving signals that are used to generate the first sound waves. As illustrated in FIG. 1, processor 150 may measure a first time-delay between the first sound waves and the first driving signals. In case the sound waves are generated in a burst fashion, processor 150 may measure the first time-delay based on the burst timing of the first driving signals and first sound waves. In some embodiments, processor 150 may include a microprocessor, a signal generator configured to generate the driving signals, an oscilloscope configured to measure and/or display the sound waves and the time delays, or a combination thereof. Block S530 may be followed by block S540, "HEATING THE HAIR TO AT LEAST PARTIALLY REMOVE MOISTURE FROM THE HAIR."

At block S540, the hair may be heated to at least partially remove moisture from the hair. As depicted in FIG. 1, heater 140 may generate heat for at least partially evaporating or removing moisture in hair 130. Hair 130 may be heated for a predetermined period of time at a predetermined temperature, which may be not greater than a temperature at which hair 130 may denature. For example, hair 130 may be heated for about 120 seconds at 60 degrees Celsius or less. In case of using a ceramic heater as heater 140, heat may be generated by passing electricity through heating wires embedded in a ceramic material, in which the electricity may be provided from processor 150. Alternatively, a heater including infrared LEDs may be used as heater 140, in which heat may be generated by providing electricity to the LEDs so that the LEDs irradiate infrared light. Block S540 may be followed by block S550, "PROPAGATING SECOND SOUND WAVES THROUGH THE AT LEAST ONE STRAND OF HAIR AFTER HEATING."

At block S550, second sound waves may be propagated through the at least one strand of hair after heating. As illustrated in FIG. 1, after heating hair 130, vibrator 110 may generate second sound waves in response to second driving signals that may be provided from processor 150, and propagate the second sound waves through the strand of hair 130. Block S550 may be followed by block S560, "DETECTING THE SECOND SOUND WAVES THAT HAVE PROPAGATED THROUGH THE HAIR."

At block S560, the second sound waves that have propagated through the hair may be detected. As illustrated in FIG. 1, sound wave detector 120 may detect the second sound waves that have propagated through hair 130. Block S560 may be followed by block S570, "MEASURING A SECOND TIME-DELAY BETWEEN THE SECOND SOUND WAVES AND SECOND DRIVING SIGNALS THAT ARE USED TO GENERATE THE SECOND SOUND WAVES."

At block S570, a second time-delay may be measured between the second sound waves and second driving signals that are used to generate the second sound waves. As depicted in FIG. 1, processor 150 may measure a second time-delay between the second sound waves and the second driving signals. Block S570 may be followed by block S580, "MEASURING AN AMOUNT OF THE MOISTURE BY CALCULATING A TIME-DELAY DIFFERENCE BETWEEN THE FIRST TIME-DELAY AND THE SECOND TIME-DELAY."

At block S580, an amount of the moisture may be measured by calculating a time-delay difference between the first time-delay and the second time-delay. As illustrated in FIG. 1, processor 150 may measure an amount of the moisture by calculating a time-delay difference between the first time-delay and the second time-delay. As such, processor 150 may measure an amount of the moisture in hair 130 by comparing the first time-delay between the first driving signals and the first sound waves, which is detected for hair 130 prior to being heated by heater 140, and the second time-delay between the second driving signals and the second sound waves, which is detected for hair 130 after being heated by heater 140.

In some embodiments, a difference between the first and second time-delays may be compared with a reference, which may be pre-stored in a memory unit of the hair moisture measuring device. The reference may include a list of time-delay differences associated with respective moisture contents. For example, a look-up table including the reference may be pre-stored in the memory unit. The reference time-delay differences and associated moisture contents may be pre-measured for predetermined exemplary hair types (for example, exemplary hair sampled from different races, different animals, etc.). The amount of moisture contained in the hair may be determined by identifying the time-delay difference in the reference that best matches the time-delay difference between the first time-delay and the second time-delay.

Figure 6:
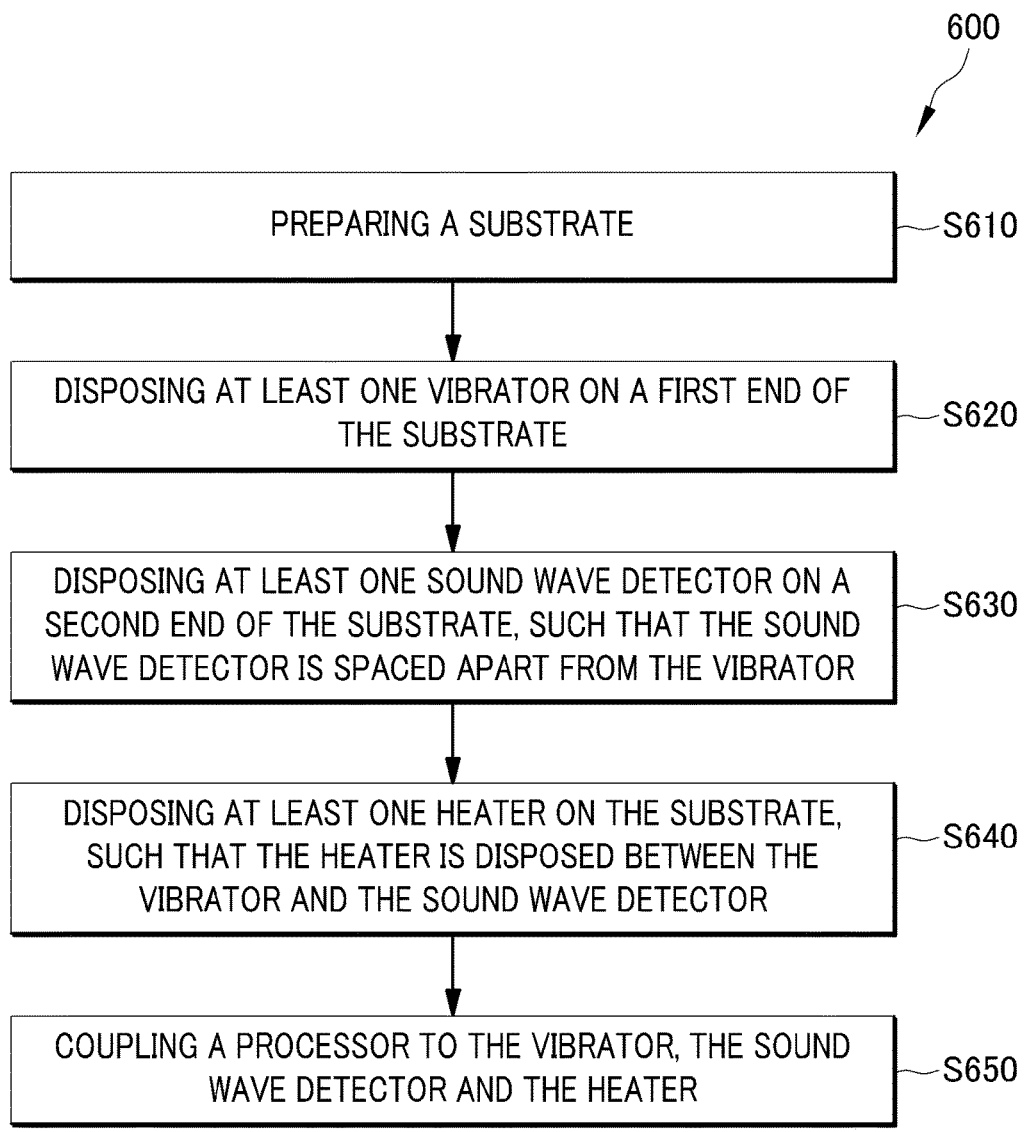
FIG. 6 illustrates an example flow diagram of a method adapted to manufacture a hair moisture measuring device.

FIG. 6 illustrates an example flow diagram of a method adapted to manufacture a hair moisture measuring device, arranged in accordance with at least some embodiments described herein. An example method 600 in FIG. 6 may be implemented using, for example, a computing device including a processor adapted to control manufacturing of a hair moisture measuring device.

Method 600 may include one or more operations, actions, or functions as illustrated by one or more of blocks S610, S620, S630, S640 and/or S650. Although illustrated as discrete blocks, various blocks may be divided into additional blocks, combined into fewer blocks, or eliminated, depending on the desired implementation. In some further examples, the various described blocks may be implemented as a parallel process instead of a sequential process, or as a combination thereof. Method 600 may begin at block S610, "PREPARING A SUBSTRATE."

At block S610, a substrate may be prepared. As illustrated in FIGS. 3A and 3B or FIGS. 4A and 4B, substrate 380 or 480 may be prepared as a member for supporting other elements including vibrator 310 or 410, sound wave detector 320 or 420, and/or first and second clamps 360 and 370 or 460 and 470. Substrate 380 or 480 may serve as an enclosure configured to accommodate a processor or any other units for controlling the operation of device 300 or 400. Block S610 may be followed by block S620, "DISPOSING AT LEAST ONE VIBRATOR ON A FIRST END OF THE SUBSTRATE."

At block 620, at least one vibrator may be disposed on a first end of the substrate. As illustrated in FIGS. 3A and 3B or FIGS. 4A and 4B, vibrator 310 or 410 may be disposed on a first end of substrate 380 or 480, which may be in the vicinity of first clamp 360 or 460. Vibrator 310 or 410 may be configured to generate sound waves in response to driving signals, and to propagate the sound waves through at least one strand of hair 330 or 430 before and after moisture removal. Block S620 may be followed by block S630, "DISPOSING AT LEAST ONE SOUND WAVE DETECTOR ON A SECOND END OF THE SUBSTRATE, SUCH THAT THE SOUND WAVE DETECTOR IS SPACED APART FROM THE VIBRATOR."

At block 630, at least one sound wave detector may be disposed on a second end of the substrate, such that the sound wave detector is spaced apart from the vibrator. As illustrated in FIGS. 3A and 3B or FIGS. 4A and 4B, sound wave detector 320 or 420 may be disposed on a second end of substrate 380 or 480, which may be in the vicinity of second clamp 370 or 470. Sound wave detector 320 or 420 may be configured to detect the sound waves that have propagated through hair 330 or 430. Block S630 may be followed by block S640, "DISPOSING AT LEAST ONE HEATER ON THE SUBSTRATE, SUCH THAT THE HEATER IS DISPOSED BETWEEN THE VIBRATOR AND THE SOUND WAVE DETECTOR."

At block 640, at least one heater may be disposed on the substrate, such that the heater is disposed between the vibrator and the sound wave detector. As depicted in FIGS. 3A and 3B or FIGS. 4A and 4B, heater 340 or 440 may be disposed on substrate 380 or 480, such that heater 340 or 440 is disposed between vibrator 310 or 410 and sound wave detector 320 or 420. Heater 340 or 440 may be configured to generate heat for at least partially removing moisture in hair 330 or 430. Block S640 may be followed by block S650, "COUPLING A PROCESSOR TO THE VIBRATOR, THE SOUND WAVE DETECTOR AND THE HEATER."

At block S650, a processor may be coupled to the vibrator, the sound wave detector and the heater. As depicted in FIGS. 3A and 3B or FIGS. 4A and 4B, a processor embedded in substrate 380 or 480 may be electrically coupled to vibrator 310 or 410, sound wave detector 320 or 420 and heater 340 and 440. The processor may be configured to generate the driving signals that are fed to vibrator 310 or 410, and to measure a time-delay between the sound waves and the driving signals. In some embodiments, the processor may be further configured to measure an amount of moisture in hair 330 or 430 by comparing a first time-delay between the sound waves and the driving signals associated with hair 330 or 430 prior to being heated by heater 340 or 440, and a second time-delay between the sound waves and the driving signals associated with hair 330 or 430 after being heated by heater 340 or 440.

In some embodiments, a first clamp such as first clamp 360 or 460 may be further disposed on the first end of the substrate, the first clamp being configured to clamp a first end of the hair. Also, a second clamp such as second clamp 370 or 470 may be disposed on the second end of the substrate, the second clamp being configured to clamp a second end of the hair. In this configuration, the hair may be stretched between the first clamp and the second clamp, and the hair may be coupled to the vibrator and to the sound wave detector. Further, a display unit may be coupled to the processor, the display unit being configured to display at least one of the driving signals, the sound waves, and the measured time delays.

In light of the present disclosure, one skilled in the art will appreciate that, for this and other methods disclosed herein, the functions performed in the methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 7:
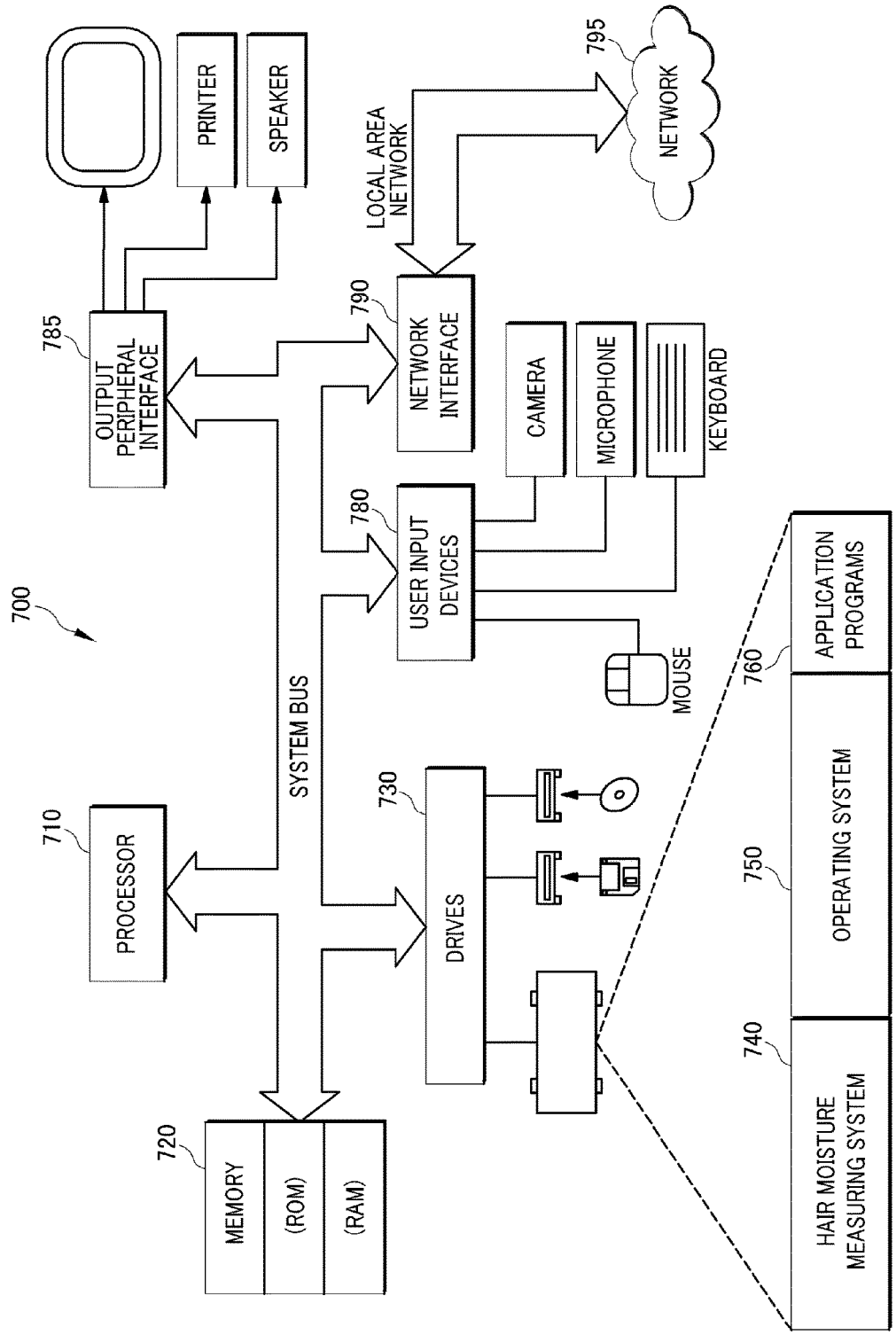
FIG. 7 shows a schematic block diagram illustrating an example computing system that can be configured to implement methods for measuring hair moisture.

FIG. 7 shows a schematic block diagram illustrating an example computing system that can be configured to implement methods for measuring hair moisture, arranged in accordance with at least some embodiments described herein. As depicted in FIG. 7, a computer 700 may include a processor 710, a memory 720 and one or more drives 730. Computer 700 may be implemented as a conventional computer system, an embedded control computer, a laptop, or a server computer, a mobile device, a set-top box, a kiosk, a vehicular information system, a mobile telephone, a customized machine, or other hardware platform.

Drives 730 and their associated computer storage media may provide storage of computer readable instructions, data structures, program modules and other data for computer 700. Drives 730 may include a hair moisture measuring system 740, an operating system (OS) 750, and application programs 760. Hair moisture measuring system 740 may be adapted to control a hair moisture measuring device in such a manner as described above with respect to FIGS. 1 to 6.

Computer 700 may further include user input devices 780 through which a user may enter commands and data. Input devices can include an electronic digitizer, a camera, a microphone, a keyboard and pointing device, commonly referred to as a mouse, trackball or touch pad. Other input devices may include a joystick, game pad, satellite dish, scanner, or the like.

These and other input devices can be coupled to processor 710 through a user input interface that is coupled to a system bus, but may be coupled by other interface and bus structures, such as a parallel port, game port or a universal serial bus (USB). Computers such as computer 700 may also include other peripheral output devices such as display devices, which may be coupled through an output peripheral interface 785 or the like.

Computer 700 may operate in a networked environment using logical connections to one or more computers, such as a remote computer coupled to a network interface 790. The remote computer may be a personal computer, a server, a router, a network PC, a peer device or other common network node, and can include many or all of the elements described above relative to computer 700.

Networking environments are commonplace in offices, enterprise-wide area networks (WAN), local area networks (LAN), intranets, and the Internet. When used in a LAN or WLAN networking environment, computer 700 may be coupled to the LAN through network interface 790 or an adapter. When used in a WAN networking environment, computer 700 typically includes a modem or other means for establishing communications over the WAN, such as the Internet or a network 795. The WAN may include the Internet, the illustrated network 795, various other networks, or any combination thereof. It will be appreciated that other mechanisms of establishing a communications link, ring, mesh, bus, cloud, or network between the computers may be used.

In some embodiments, computer 700 may be coupled to a networking environment. Computer 700 may include one or more instances of a physical computer-readable storage medium or media associated with drives 730 or other storage devices. The system bus may enable processor 710 to read code and/or data to/from the computer-readable storage media. The media may represent an apparatus in the form of storage elements that are implemented using any suitable technology, including but not limited to semiconductors, magnetic materials, optical media, electrical storage, electrochemical storage, or any other such storage technology. The media may represent components associated with memory 720, whether characterized as RAM, ROM, flash, or other types of volatile or nonvolatile memory technology. The media may also represent secondary storage, whether implemented as storage drives 730 or otherwise. Hard drive implementations may be characterized as solid state, or may include rotating media storing magnetically encoded information.

Processor 710 may be constructed from any number of transistors or other circuit elements, which may individually or collectively assume any number of states. More specifically, processor 710 may operate as a state machine or finite-state machine. Such a machine may be transformed to a second machine, or specific machine by loading executable instructions. These computer-executable instructions may transform processor 710 by specifying how processor 710 transitions between states, thereby transforming the transistors or other circuit elements constituting processor 710 from a first machine to a second machine. The states of either machine may also be transformed by receiving input from user input devices 780, network interface 790, other peripherals, other interfaces, or one or more users or other actors. Either machine may also transform states, or various physical characteristics of various output devices such as printers, speakers, video displays, or otherwise.

Figure 8:
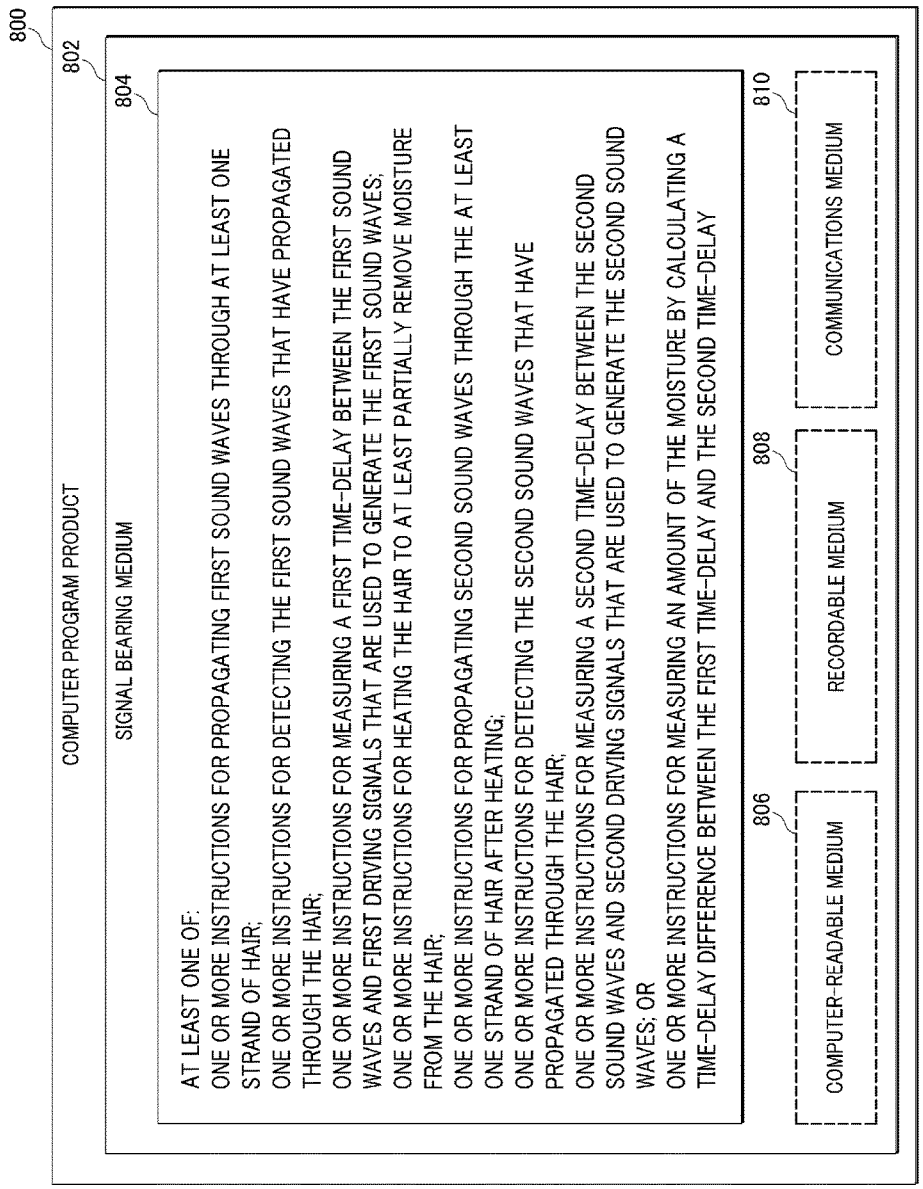
FIG. 8 illustrates computer program products that can be utilized to measure hair moisture, all arranged in accordance with at least some embodiments described herein.

FIG. 8 illustrates computer program products that can be utilized to measure hair moisture, in accordance with at least some embodiments described herein. Program product 800 may include a signal bearing medium 802. Signal bearing medium 802 may include one or more instructions 804 that, when executed by, for example, a processor, may provide the functionality described above with respect to FIGS. 1 to 6. By way of example, instructions 804 may include at least one of: one or more instructions for propagating first sound waves through at least one strand of hair; one or more instructions for detecting the first sound waves that have propagated through the hair; one or more instructions for measuring a first time-delay between the first sound waves and first driving signals that are used to generate the first sound waves; one or more instructions for heating the hair to at least partially remove moisture from the hair; one or more instructions for propagating second sound waves through the at least one strand of hair after heating; one or more instructions for detecting the second sound waves that have propagated through the hair; one or more instructions for measuring a second time-delay between the second sound waves and second driving signals that are used to generate the second sound waves; or one or more instructions for measuring an amount of the moisture by calculating a time-delay difference between the first time-delay and the second time-delay. Thus, for example, referring to FIGS. 1 to 4B, hair moisture measuring device 100, 200, 300 or 400 may undertake one or more of the blocks shown in FIG. 5 in response to instructions 804.

In some implementations, signal bearing medium 802 may encompass a computer-readable medium 806, such as, but not limited to, a hard disk drive, a Compact Disc (CD), a Digital Video Disk (DVD), a digital tape, memory, etc. In some implementations, signal bearing medium 802 may encompass a recordable medium 808, such as, but not limited to, memory, read/write (R/W) CDs, R/W DVDs, etc. In some implementations, signal bearing medium 802 may encompass a communications medium 810, such as, but not limited to, a digital and/or an analog communication medium (for example, a fiber optic cable, a waveguide, a wired communications link, a wireless communication link, etc.). Thus, for example, program product 800 may be conveyed to one or more modules of hair moisture measuring device 100, 200, 300 or 400 by an RF signal bearing medium 802, where the signal bearing medium 802 is conveyed by a wireless communications medium 810 (for example, a wireless communications medium conforming with the IEEE 802.11 standard).

EXAMPLES

The present disclosure will be understood more readily by reference to the following examples, which are provided by way of illustration and are not intended to be limiting in any way.

Example 1

Measuring Moisture in Human Hair in Good and Bad Health Conditions

In one experimental example, moisture in human hair was measured by a hair moisture measuring device that has been manufactured using a configuration as illustrated in FIGS. 3A and 3B. For the purpose of determining moisture measuring parameters for human hair (typically having a thickness of about 50 µm to 150 µm), moisture was measured for example human hair with an average thickness of 100 µm in good humidity condition (that was sampled in a room with atmosphere humidity of about 60% at atmosphere temperature of about 26 Celsius degrees) and another example human hair with an average thickness of 100 µm in bad humidity condition (that was sampled in a room with atmosphere humidity of about 35% at atmosphere temperature of about 18 Celsius degrees). The example hair had a relatively bad health condition because they were treated by frequent dyeing and decoloration.

The hair moisture measuring device was operated, such that first sound waves were propagated through the strand of hair to detect the first sound waves that have propagated through the example hair. The length of the example hair, which was coupled between an output of a vibrator and an input of a sound wave detector, was about 50 mm. Then, a first time-delay was measured between the first sound waves and first driving signals that are used to generate the first sound waves. Further, the example hair was heated to remove moisture from the hair for about 120 seconds at a temperature of about 60 degrees Celsius. After heating the example hair, second sound waves were propagated through the strand of hair to detect the second sound waves that have propagated through the hair. Again, a second time-delay was measured between the second sound waves and second driving signals that are used to generate the second sound waves.

The first time-delay and the second time-delay were measured for several samples of human hair with substantially same conditions (that is, a set of several hair samples with a thickness of about 100 µm in good humidity condition and another set of several hair samples with a thickness of about 100 µm in bad humidity condition). A time-delay difference between the first time-delay and the second time-delay was constantly determined to be about 2.4 µsec for the example hair in good humidity condition and about 2.0 µsec for the example hair in bad humidity condition.

According to the present disclosure, the time delay difference may be compared with a reference including a list of time-delay differences associated with respective moisture contents. As described above, the reference may be prepared by associating time delay differences with moisture contents that are measured for exemplary hair samples having different hair health conditions and/or different environments. The amount of moisture contained in the example hair may be determined by identifying a time-delay difference in the reference that best matches the time-delay difference between the first time-delay and the second time-delay. In general, the amount of moisture determined for the example hair in good health condition ranges from about 11% to 14%, while that for the example hair in bad health condition ranges from about 6% to 9%.

Example 2

Measuring Moisture in Human Hair with Fine Thickness

As discussed above, a conventional NIR moisture meter relies on the property of water that absorbs a specific wavelength of NIR light. However, it may be difficult to precisely measure the attenuation of the NIR light reflected from thin and fine hair. Contrary to the NIR moisture meter, the hair moisture measuring device according to the present disclosure was able to measure a substantially constant value of moisture in hair with fine thickness.

In one experimental example, moisture in example human hair with an average thickness of 60 μm was measured by a hair moisture measuring device that has been manufactured using a configuration as illustrated in FIGS. 3A and 3B. The length of the example hair, which was coupled between an output of a vibrator and an input of a sound wave detector, was about 50 mm. Moisture was measured for the example human hair in bad humidity condition (that was sampled in a room at atmosphere humidity of about 35% at atmosphere temperature of about 18 Celsius degrees which means low humidity condition). The example hair had a relatively good health condition because they were never treated by dyeing or decoloration. The hair moisture measuring device was operated in a similar manner as described above with respect to Example 1. The first time-delay and the second time-delay were measured several times. As a result, a time-delay difference between the first time-delay and the second time-delay was constantly determined to be about 3.0 μsec for the example hair.

The present disclosure is not to be limited in terms of the particular embodiments described in this application, which are intended as illustrations of various aspects. Many modifications and variations may be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A hair moisture measuring device, comprising:
at least one vibrator configured to generate sound waves in response to driving signals, and to propagate the sound waves through at least one strand of hair before and after moisture removal;
at least one sound wave detector spaced apart from the vibrator, configured to detect the sound waves that have propagated through the hair;
at least one heater configured to generate heat for at least partially removing moisture in the hair; and
a processor configured to generate the driving signals that are fed to the vibrator, to measure a first time-delay between the sound waves and the driving signals associated with the hair prior to being heated by the heater, to measure a second time-delay between the sound waves and the driving signals associated with the hair after being heated by the heater, and to determine an amount of removed moisture by comparing a hair time-delay difference between the first time-delay and the second time-delay to a reference.

2. The device of claim 1, wherein the vibrator comprises an ultrasonic vibrator configured to generate ultrasonic sound waves.

3. The device of claim 2, wherein the ultrasonic vibrator is an ultrasonic ceramic transducer.

4. The device of claim 1, wherein the sound wave detector comprises an ultrasonic microphone configured to detect ultrasonic sound waves.

5. The device of claim 4, wherein the ultrasonic microphone is an ultrasonic ceramic transducer.

6. The device of claim 1, wherein the heater comprises a ceramic material and at least one heating wire embedded in the ceramic material.

7. The device of claim 1, wherein the heater comprises at least one infrared LED (light-emitting diode).

8. The device of claim 1, wherein the heater comprises at least two sheets of polyimide and at least one heating wire embedded between the two sheets.

9. The device of claim 1, further comprising:
a first clamp disposed at a first end of the device and configured to clamp a first end of the hair; and
a second clamp disposed at a second end of the device and configured to clamp a second end of the hair, so that the hair is stretched between the first clamp and the second clamp, and the hair is coupled to the vibrator and to the sound wave detector.

10. The device of claim 1, wherein:
the reference includes a list of reference time-delay differences associated with exemplary hair types; and
comparing the hair time-delay difference between the first time-delay and the second time-delay to the reference includes identifying a reference time-delay difference from the list of reference time-delay differences that matches the hair time-delay difference.

11. The device of claim 1, wherein the processor comprises an oscilloscope, a microcomputer or both.

12. The device of claim 1, further comprising a display unit configured to display at least one of the driving signals, the sound waves, and the hair time-delay difference.

13. A method to measure hair moisture, the method comprising:
propagating first sound waves through at least one strand of hair;
detecting the first sound waves that have propagated through the hair;
measuring a first time-delay between the first sound waves and first driving signals that are used to generate the first sound waves;
after propagating the first sound waves, heating the hair to at least partially remove moisture from the hair;
propagating second sound waves through the at least one strand of hair after heating;
detecting the second sound waves that have propagated through the hair;
measuring a second time-delay between the second sound waves and second driving signals that are used to generate the second sound waves; and
determining an amount of removed moisture by calculating a hair time-delay difference between the first time-delay and the second time-delay and comparing the hair time-delay difference to a reference.

14. The method of claim 13, wherein generating the first sound waves and generating the second sound waves each comprises generating using at least one vibrator.

15. The method of claim 13, wherein detecting the first sound waves and the second sound waves each comprises detecting using an ultrasonic microphone.

16. The method of claim 13, wherein heating the hair comprises heating the hair using a ceramic material and heating wires embedded in the ceramic material, and passing electricity through the heating wires embedded in the ceramic material.

17. The method of claim 13, wherein heating the hair comprises heating the hair using one or more infrared LEDs, and activating the infrared LEDs to generate infrared light rays.

18. The method of claim 13, further comprising:
coupling a first end of at least one strand of hair to a vibrator; and
coupling a second end of the at least one strand of hair to a sound wave detector.

19. The method of claim 18, wherein coupling the first end of the at least one strand of hair comprises clamping the first end using a first clamp disposed adjacent to the vibrator.

20. The method of claim 18, wherein coupling the second end of the at least one strand of hair comprises clamping the second end using a second clamp disposed adjacent to the sound wave detector.

21. The method of claim 13, wherein determining the amount of the moisture comprises operating an oscilloscope configured to measure the first time-delay and the second time-delay.

22. The method of claim 13, wherein:
the reference comprises a list of time-delay differences associated respective moisture contents; and determining the amount of removed moisture by comparing the hair time-delay difference to the reference includes identifying the time-delay difference in the reference that best matches the time-delay difference between the first time-delay and the second time-delay.

23. The method of claim 13, further comprising:
generating the first driving signals for generating the first sound waves; and
generating the second driving signals for generating the second sound waves.

24. A non-transitory computer-readable storage medium which stores a program operable by a hair moisture measuring device, the program comprising one or more instructions for:
propagating first sound waves through at least one strand of hair;
detecting the first sound waves that have propagated through the hair;
measuring a first time-delay between the first sound waves and first driving signals that are used to generate the first sound waves;
heating the hair to at least partially remove moisture from the hair;
propagating second sound waves through at least one strand of hair after heating;
detecting the second sound waves that have propagated through the hair;
measuring a second time-delay between the second sound waves and second driving signals that are used to generate the second sound waves; and
determining an amount of removed moisture by calculating a hair time-delay difference between the first time-delay and second time-delay and comparing the hair time-delay difference to a reference.

25. The medium of claim 24, wherein the program further comprises one or more instructions for:
coupling a first end of at least one strand of hair to a vibrator; and
coupling a second end of the at least one strand of hair to a sound wave detector.

26. The medium of claim 24, wherein the program further comprises one or more instructions for:
generating the first driving signals for generating the first sound waves; and generating the second driving signals for generating the second sound waves.

27. A method of manufacturing a hair moisture measuring device, the method comprising:
preparing a substrate;
disposing at least one vibrator on a first end of the substrate, the vibrator being configured to generate sound waves in response to driving signals, and to propagate the sound waves through at least one strand of hair before and after moisture removal;
disposing at least one sound wave detector on a second end of the substrate, such that the sound wave detector is spaced apart from the vibrator, the sound wave detector being configured to detect the sound waves that have propagated through the hair;
disposing at least one heater on the substrate, such that the heater is disposed between the vibrator and the sound wave detector, the heater being configured to generate heat for at least partially removing moisture in the hair; and
coupling a processor to the vibrator, the sound wave detector, and the heater, the processor being configured to generate the driving signals that are fed to the vibrator, to measure a first time-delay between the sound waves and the driving signals associated with hair prior to being heated by the heater, measure a second time-delay between the sound waves and the driving signals associated with the hair after being heated by the heater, and to determine an amount of removed moisture by comparing a hair time-delay difference between the first time-delay and the second time-delay to a reference.

28. The method of claim 27, wherein disposing at least one vibrator comprises disposing at least one ultrasonic vibrator configured to generate ultrasonic sound waves.

29. The method of claim 27, wherein disposing at least one sound wave detector comprises disposing at least one ultrasonic microphone configured to detect ultrasonic sound waves.

30. The method of claim 27, wherein disposing the at least one heater comprises disposing at least one ceramic material and at least one heating wire embedded in the ceramic material.

31. The method of claim 27, wherein disposing the at least one heater comprises disposing at least one infrared LED.

32. The method of claim 27, further comprising:
disposing a first clamp on the first end of the substrate, the first clamp being configured to clamp a first end of the hair; and
disposing a second clamp on the second end of the substrate, the second clamp being configured to clamp a second end of the hair, so that the hair is stretched between the first clamp and the second clamp, and the hair is coupled to the vibrator and to the sound wave detector.

33. The method of claim 27, wherein coupling the processor comprises coupling an oscilloscope, a microcomputer or both.

34. The method of claim 27, further comprising coupling a display unit to the processor, the display unit being configured to display at least one of the driving signals, the sound waves, and the hair time-delay difference.

* * * * *